United States Patent
Chen (10) Patent No.: US 9,567,571 B2
(45) Date of Patent: Feb. 14, 2017

(54) HEPATITIS B VIRUS MUTANT, MUTANT AMPLIFICATION KIT AND USE THEREOF

(75) Inventor: Zhi Chen, Zhejiang (CN)

(73) Assignee: ZHEJIANG UNIVERSITY, Xihu District, Hangzhou, Zhejiang (CN)

( * ) Notice: Subject to any disclaimer, the term of this patent is extended or adjusted under 35 U.S.C. 154(b) by 0 days.

(21) Appl. No.: 14/360,931

(22) PCT Filed: Feb. 14, 2012

(86) PCT No.: PCT/CN2012/071108
§ 371 (c)(1),
(2), (4) Date: Aug. 18, 2014

(87) PCT Pub. No.: WO2013/078786
PCT Pub. Date: Jun. 6, 2013

(65) Prior Publication Data
US 2015/0284690 A1    Oct. 8, 2015

(30) Foreign Application Priority Data
Nov. 28, 2011    (CN) .......................... 2011 1 0384731

(51) Int. Cl.
*C12N 7/00*    (2006.01)
*C12P 19/34*    (2006.01)
*C12Q 1/70*    (2006.01)

(52) U.S. Cl.
CPC ................. *C12N 7/00* (2013.01); *C12P 19/34* (2013.01); *C12Q 1/706* (2013.01); *C12N 2710/00021* (2013.01); *C12N 2730/10121* (2013.01); *C12Q 2600/156* (2013.01)

(58) Field of Classification Search
CPC .... A61K 38/00; A61K 31/7088; A61K 39/12; C12Q 1/6844; C12Q 1/6869; C12Q 1/6816; C12Q 2600/118; C12Q 1/6827; C12Q 1/70; C12Q 1/706; C12Q 2600/112; C12N 7/00; C12N 2730/10131; G01N 2800/52; G01N 2800/50; G01N 33/56983
See application file for complete search history.

(56) References Cited

U.S. PATENT DOCUMENTS 7,439,016 B1 * 10/2008 Anthony .............. C12Q 1/6834
435/6.1

FOREIGN PATENT DOCUMENTS

JP       2002355098 A  * 12/2002
WO      WO2005042733    *  5/2005

OTHER PUBLICATIONS

Weber B. Genetic variability of the S gene of hepatitis B virus: clinical and diagnostic impact. J Clin Virol. Feb. 2005;32(2):102-12.*

Zhang ZH, Li L, Zhao XP, Glebe D, Bremer CM, Zhang ZM, Tian YJ, Wang BJ, Yang Y, Gerlich W, Roggendorf M, Li X, Lu M, Yang DL. Elimination of hepatitis B virus surface antigen and appearance of neutralizing antibodies in chronically infected patients without viral clearance. J Viral Hepat. Jun. 2011;18(6):424-33. Epub Aug. 31, 2010.*

Teshale EH, Ramachandran S, Xia GL, Roberts H, Groeger J, Barry V, Hu DJ, Holmberg SD, Holtzman D, Ward JW, Teo CG, Khudyakov Y. Genotypic distribution of hepatitis B virus (HBV) among acute cases of HBV infection, selected United States counties, 1999-2005. Clin Infect Dis. Oct. 2011;53(8):751-6. Epub Aug. 22, 2011.*

Kumar GT, Kazim SN, Kumar M, Hissar S, Chauhan R, Basir SF, Sarin SK. Hepatitis B virus genotypes and hepatitis B surface antigen mutations in family contacts of hepatitis B virus infected patients with occult hepatitis B virus infection. J Gastroenterol Hepatol. Apr. 2009;24(4):588-98. Epub Jan. 13, 2009.*

Fang Y, Teng X, Xu WZ, Li D, Zhao HW, Fu LJ, Zhang FM, Gu HX. Molecular characterization and functional analysis of occult hepatitis B virus infection in Chinese patients infected with genotype C. J Med Virol. May 2009;81(5):826-35.*

Fang Y, Gu H. Hepatitis B virus isolate S4.3, complete genome. GenBank Dep. No. EU916217.1. Dep. Apr. 9, 2009.*

Ren X, Xu Z, Liu Y, Li X, Dai J, Zhong Y, Xu D. Hepatitis B virus isolate D36, complete genome. GenBank Dep. No. EU939644.1. Aug. 31, 2008.*

Takara Bio Inc., PrimeSTAR® GLX DNA Polymerase. Product Manual. Updated and published Sep. 1, 2011. http://www.clontech.com/US/Products/PCR/GC_Rich/PrimeSTAR_GXL_DNA_Polymerase.*

* cited by examiner

*Primary Examiner* — Rachel B Gill
(74) *Attorney, Agent, or Firm* — Global IP Services; Tianhua Gu (57) ABSTRACT

The present invention relates to the field of biotechnology, and discloses a hepatitis B virus mutant, a mutant amplification kit and use thereof. The HBV mutant of the invention takes place mutation of the hepatitis B virus mutant in genome sequence No. 216 and/or 285, the mutation occurred at position 216 is that base T mutates to C, the mutation occurred at position 285 is that base G mutates to A. The two mutations are closely related to the inflammation aggravation of the hepatitis B. The invention further provides a HBV mutant amplification kit to detect the above mutation, the usage of the kit and its application, therefore offering help for the clinical early diagnosis and intervention of severe hepatitis B, and providing references for further studying the functional changes caused by HBV gene mutation.

6 Claims, 1 Drawing Sheet

SEQUENCE LISTING

<160> NUMBER OF SEQ ID NOS: 12

<210> SEQ ID NO 1
<211> LENGTH: 3215
<212> TYPE: DNA
<213> ORGANISM: Hepatitis B virus

<400> SEQUENCE: 1

| | | | | | |
|---|---|---|---|---|---|
| ctccacaaca | ttccaccaag | ctctgctaga | ccccagagtg | aggggcctat | actttcctgc | 60 |
| tggtggctcc | agttccggaa | cagtaaaccc | tgttccgact | actgcctcac | ccatatcgtc | 120 |
| aatcttctcg | aggactgggg | accctgcacc | gaacatggag | aacacaacat | caggattcct | 180 |
| aggaccctg | ctcgtgttac | aggcggggtt | tttcttgttg | acaagaatcc | tcacaatacc | 240 |
| acagagtcta | gactcgtggt | ggacttctct | caattttcta | gggggagcac | ccacgtgtcc | 300 |
| tggccaaaat | tcgcagtccc | caacctccaa | tcactcacca | acctcttgtc | ctccaatttg | 360 |
| tcctggctat | cgctggatgt | gtctgcggcg | ttttatcata | ttcctcttca | tcctgctgct | 420 |
| atgcctcatc | ttcttgttgg | ttcttctgga | ctaccaaggt | atgttgcccg | tttgtcctct | 480 |
| acttccagga | acatcaacta | ccagcacggg | accatgcaag | acctgcacga | ttcctgctca | 540 |
| aggaacctct | atgtttccct | cttgttgctg | tacaaaacct | tcggacggaa | actgcacttg | 600 |
| tattcccatc | ccatcatcct | gggctttcgc | aagattccta | tgggagtggg | cctcagtccg | 660 |
| tttctcctgg | ctcagtttac | tagtgccatt | tgttcagtgg | ttcgtagggc | tttcccccac | 720 |
| tgtttggctt | tcagttatat | ggatgatgtg | gtattggggg | ccaagtctgt | acaacatctt | 780 |
| gagtcccttt | ttacctctat | taccaatttt | cttttgtctt | tgggtataca | tttgaaccct | 840 |
| aataaaacca | aacgttgggg | ctactccctt | aacttcatgg | gatatgtaat | ggaagttgg | 900 |
| ggtactttac | cgcaagaaca | tattgtacta | aaaatcaagc | aatgttttcg | aaaactgcct | 960 |
| gtaaatagac | ctattgattg | gaaagtatgt | cagagaattg | tgggtctttt | gggctttgct | 1020 |
| gccccttta | cacaatgtgg | ctatcctgcc | ttaatgcctt | tatatgcatg | tatacaatct | 1080 |
| aagcaggctt | tcactttctc | gccaacttac | aaggcctttc | tgtgtaaaca | atatctgaac | 1140 |
| ctttacccg | ttgcccggca | acggtcaggt | ctctgccaag | tgtttgctga | cgcaaccccc | 1200 |
| actggatggg | gcttggctat | tggccatcgg | cgcatgcgtg | gaacctttgt | ggctcctctg | 1260 |
| ccgatccata | ctgcggaact | cctagcagct | tgttttgctc | gcagccggtc | tggagcgaaa | 1320 |
| cttatcggaa | ccgacaactc | tgttgtcctc | tctcggaaat | acacctcctt | tccatggctg | 1380 |
| ctagggtgtg | ctgccaactg | gatcctgcgc | gggacgtcct | ttgtctacgt | cccgtcggcg | 1440 |
| ctgaatcccg | cggacgaccc | gtctcggggc | cgtttgggac | tctaccgtcc | ccttcttcat | 1500 |
| ctgccgttcc | ggccgaccac | ggggcgcacc | tctctttacg | cggtctcccc | gtctgtgcct | 1560 |
| tctcatctgc | cggaccgtgt | gcacttcgct | tcacctctgc | acgtcgcatg | gagaccaccg | 1620 |
| tgaacgccca | ccaggtcttg | cccaaggtct | tacataagag | gactcttgga | ctctcagcaa | 1680 |
| tgtcaacgac | cgaccttgag | gcatacttca | aagactgttt | gtttaaggac | tgggaggagt | 1740 |
| tgggggagga | gattaggtta | atgatctttg | tactaggagg | ctgtaggcat | aaattggtct | 1800 |
| gttcaccagc | accatgcaac | ttttcacct | ctgcctaatc | atctcatgtt | catgtcctac | 1860 |
| tgttcaagcc | tccaagctgt | gccttgggtg | gctttgggc | atggacattg | acccgtataa | 1920 |
| agaatttgga | gcttctgtgg | agttactctc | tttttgcct | tctgacttct | ttccttctat | 1980 |
| tcgagatctc | ctcgacaccg | cctctgctct | gtatcgggag | gccttagagt | ctccggaaca | 2040 |
| ttgttcacct | caccatacag | cactcaggca | agctattctg | tgttggggtg | agttgatgaa | 2100 |

```
tctggccacc tgggtgggaa gtaatttgga agacccagca tccagggaat tagtagtcag    2160
ctatgtcaat gttaatatgg gcctaaaaat cagacaacta ctgtggtttc acatttcctg    2220
tcttactttt ggaagagaaa ctgttcttga gtatttggtg tcttttggag tgtggattcg    2280
cactcctcct gcttacagac caccaaatgc ccctatctta tcaacacttc cggaaactac    2340
tgttgttaga cgacgaggca ggtcccctag aagaagaact ccctcgcctc gcagacgaag    2400
gtctcaatcg ccgcgtcgca gaagatctca atctcgggaa tctcaatgtt agtatcccct    2460
ggactcataa ggtgggaaac tttactgggc tttattcttc tactgtacct gtctttaatc    2520
ctgagtggca aactccctcc tttcctcaca ttcatttaca ggaggacatt attaatagat    2580
gtcaacaata tgtgggccct cttacagtta atgaaaaaag gagattaaaa ttaattatgc    2640
ctgctaggtt ctatcctaac cttaccaaat atttgcccctt ggacaaaggc attaaaccat    2700
attatcctga acatgcagtt aatcattact tcaaaactag gcattattta catactctgt    2760
ggaaggctgg cattctatat aagagagaaa ctacacgcag cgcctcattt tgtgggtcac    2820
catattcttg gaacaagag ctacagcatg ggaggttggt cttccaaacc tcgacaaggc    2880
atggggacga atctttctgt tcccaatcct ctgggattct ttcccgatca ccagttggac    2940
cctgcgttcg gagccaactc aaacaatcca gattgggact tcaaccccaa caaggatcac    3000
tggccagagg caaatcaggt aggagcggga gcattcgggc cagggttcac cccaccacac    3060
ggcggtcttt tggggtggag ccctcaggct cagggcatat tgacaacagt gccagtagca    3120
cctcctcctg cctccaccaa tcggcagtca ggaagacagc ctactcccat ctctccacct    3180
ctaagagaca gtcatcctca ggccatgcag tggaa                              3215
```

<210> SEQ ID NO 2
<211> LENGTH: 19
<212> TYPE: DNA
<213> ORGANISM: Artificial
<220> FEATURE:
<223> OTHER INFORMATION: Primer

<400> SEQUENCE: 2
agtgggcctc agtccgttt                                                 19

<210> SEQ ID NO 3
<211> LENGTH: 22
<212> TYPE: DNA
<213> ORGANISM: Artificial
<220> FEATURE:
<223> OTHER INFORMATION: Primer

<400> SEQUENCE: 3
aaaaagttgc atggtgctgg tg                                             22

<210> SEQ ID NO 4
<211> LENGTH: 25
<212> TYPE: DNA
<213> ORGANISM: Artificial
<220> FEATURE:
<223> OTHER INFORMATION: Primer

<400> SEQUENCE: 4
aacgaccgac cttgaggcat acttc                                          25

<210> SEQ ID NO 5
<211> LENGTH: 22
<212> TYPE: DNA

```
<213> ORGANISM: Artificial
<220> FEATURE:
<223> OTHER INFORMATION: Primer

<400> SEQUENCE: 5
gttcccaaga atatggtgac cc                                              22

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
aatctcggga atctcaatgt tag                                             23

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
agggactcaa gatgttgtac agact                                           25

<210> SEQ ID NO 8
<211> LENGTH: 17
<212> TYPE: DNA
<213> ORGANISM: Artificial
<220> FEATURE:
<223> OTHER INFORMATION: Primer

<400> SEQUENCE: 8
ggagcgggag cattcgg                                                    17

<210> SEQ ID NO 9
<211> LENGTH: 25
<212> TYPE: DNA
<213> ORGANISM: Artificial
<220> FEATURE:
<223> OTHER INFORMATION: Primer

<400> SEQUENCE: 9
ataaaacgcc gcagasacat ccagc                                           25

<210> SEQ ID NO 10
<211> LENGTH: 3215
<212> TYPE: DNA
<213> ORGANISM: Hepatitis B virus

<400> SEQUENCE: 10
ctccacaaca ttccaccaag ctctgctaga ccccagagtg aggggcctat actttcctgc     60
tggtggctcc agttccggaa cagtaaaccc tgttccgact actgcctcac ccatatcgtc    120
aatcttctcg aggactgggg accctgcacc gaacatggag aacacaacat caggattcct    180
aggacccctg ctcgtgttac aggcggggtt tttcttgttg acaagaatcc tcacaatacc    240
acagagtcta gactcgtggt ggacttctct caattttcta gggggagcac ccacgtgtcc    300
tggccaaaat tcgcagtccc caacctccaa tcactcacca acctcttgtc ctccaatttg    360
tcctggctat cgctggatgt gtctgcggcg ttttatcata ttcctcttca tcctgctgct    420
atgcctcatc ttcttgttgg ttcttctgga ctaccaaggt atgttgcccg tttgtcctct    480
```

```
acttccagga acatcaacta ccagcacggg accatgcaag acctgcacga ttcctgctca    540
aggaacctct atgtttccct cttgttgctg tacaaaacct tcggacggaa actgcacttg    600
tattcccatc ccatcatcct gggctttcgc aagattccta tgggagtggg cctcagtccg    660
tttctcctgg ctcagtttac tagtgccatt tgttcagtgg ttcgtagggc tttcccccac    720
tgtttggctt tcagttatat ggatgatgtg gtattggggg ccaagtctgt acaacatctt    780
gagtcccttt ttacctctat taccaatttt cttttgtctt tgggtataca tttgaaccct    840
aataaaacca aacgttgggg ctactccctt aacttcatgg gatatgtaat tggaagttgg    900
ggtactttac cgcaggaaca tattgtacta aaactcaagc aatgttttcg aaaactgcct    960
gtaaatagac ctattgattg gaaagtatgt caaagaattg tgggtctttt gggctttgct   1020 gccccttta cacaatgtgg ctatcctgcc ttaatgcctt tatatgcatg tatacaatct   1080
aagcaggctt tcactttctc gccaacttac aaggcctttc tgtgtaaaca atatctgaac   1140
ctttaccccg ttgcccggca acggtcaggt ctctgccaag tgtttgctga cgcaacccccc   1200 actggatggg gcttggccat aggccatcgg cgcatgcgtg gaacctttgt ggctcctctg   1260
ccgatccata ctgcggaact cctagcagct tgttttgctc gcagccggtc tggagcgaaa   1320
cttatcggaa ccgacaactc tgttgtcctc tctcggaaat acacctcctt tccatggctg   1380
ctagggtgtg ctgccaactg gatcctgcgc gggacgtcct ttgtctacgt cccgtcggcg   1440
ctgaatcccg cggacgaccc gtctcggggc cgtttgggac tctaccgtcc ccttcttcat   1500
ctgccgttcc ggccgaccac ggggcgcacc tctctttacg cggtctcccc gtctgtgcct   1560
tctcatctgc cggaccgtgt gcacttcgct tcacctctgc acgtcgcatg gagaccaccg   1620
tgaacgccca ccaggtcttg cccaaggtct tacataagag gactcttgga ctctcagcaa   1680
tgtcaacgac cgaccttgag gcatacttca aagactgttt gtttaaagac tgggaggact   1740
tgggggagga gattaggtta atgatctttg tactaggagg ctgtaggcat aaattggtct   1800
gttcaccagc accatgcaac ttttttcacct ctgcctaatc atctcatgtt catgtcctac   1860
tgttcaagcc tccaagctgt gccttgggtg gctttgggc atggacattg acccgtataa   1920
agaatttgga gcttctgtgg agttactctc ttttttgcct tctgacttct ttccttctat   1980
tcgagatctc ctcgacaccg cctctgctct gtatcgggag gccttagagt ctccggaaca   2040
ttgttcacct caccatacag cactcaggca agctattctg tgttggggtg agttgatgaa   2100
tctggccacc tgggtgggaa gtaatttgga agacccagca tccagggaat tagtagtcag   2160
ctatgtcaat gttaatatgg gcctaaaaat cagacaacta ttgtggtttc acatttcctg   2220
tcttactttt ggaagagaaa ctgttcttga gtatttggtg tcttttggag tgtggattcg   2280
cactcctccc gcttacagac caccaaatgc ccctatctta tcaacacttc cggaaactac   2340
tgttgttaga cgacgaggca ggtcccctag aagaagaact ccctcgcctc gcagacgaag   2400
gtctcaatcg ccgcgtcgca gaagatctca atctcgggaa tctcaatgtt agtatcccctt   2460 ggactcataa ggtgggaaac tttactgggc tttattcttc tactgtacct gtctttaatc   2520
ctgagtggca aactccctcc tttcctcaca ttcatttaca ggaggacatt attaatagat   2580
gtcaacaata tgtgggccct cttacagtta atgaaaaaag gagattaaaa ttaattatgc   2640
ctgctaggtt ctatcctaac cttaccaaat atttgcccct tggacaaggc attaaaccgt   2700
attatcctga acatgcagtt aatcattact tcaaaactag gcattattta catactctgt   2760
ggaaggctgg cattctatat aagagagaaa ctacacgcag cgcctcattt tgtgggtcac   2820
```

| | |
|---|---|
| catattcttg ggaacaagag ctacagcatg ggaggttggt cttccaaacc tcgacaaggc | 2880 |
| atggggacga atctttctgt tcccaatcct ctgggattct ttcccgatca ccagttggac | 2940 |
| cctgcgttcg gagccaactc aaacaatcca gattgggact tcaaccccaa caaggatcac | 3000 |
| tggccagagg caaatcaggt aggagcggga gcattcgggc cagggttcac cccaccacac | 3060 |
| ggcggtcttt tggggtggag ccctcaggct cagggcatat tgacaacagt gccagcagca | 3120 |
| cctcctcctg cctccaccaa tcggcagtca ggaagacagc ctactcccat ctctccacct | 3180 |
| ctaagagaca gtcatcctca ggccatgcag tggaa | 3215 |

<210> SEQ ID NO 11
<211> LENGTH: 3215
<212> TYPE: DNA
<213> ORGANISM: Hepatitis B virus

<400> SEQUENCE: 11

| | |
|---|---|
| ctccaccact ttccaccaaa ctcttcaaga tcccagagtc agggccctgt actttcctgc | 60 |
| tggtggctcc agttcaggaa cagtgagccc tgctcagaat actgtctctg ccatatcgtc | 120 |
| aatcttatcg aagactgggg accctgtacc gaacatggag aacatcgcat caggactcct | 180 |
| aggacccctg ctcgtgttac aggcggggtt tttcttgttg acaaaaatcc tcacaatacc | 240 |
| acagagtcta gactcgtggt ggacttctct caattttcta gggggaacac ccgtgtgtct | 300 |
| tggccaaaat tcgcagtccc aaatctccag tcactcacca acctgttgtc ctccaatttg | 360 |
| tcctggttat cgctggatgt gtctgcggcg ttttatcatc ttcctctgca tcctgctgct | 420 |
| atgcctcatc ttcttgttgg ttcttctgga ctatcaaggt atgttgcccg tttgtcctct | 480 |
| aattccagga tcatcaacaa ccagcaccgg accatgcaaa acctgcacaa ctcctgctca | 540 |
| aggaacctct atgtttccct catgttgctg tacaaaacct acggacggaa actgcacctg | 600 |
| tattcccatc ccatcatctt gggctttcgc aaaataccta tgggagtggg cctcagtccg | 660 |
| tttctcttgg ctcagtttac tagtgccatt tgttcagtgg ttcgtagggc tttcccccac | 720 |
| tgtctggctt tcagttatat ggatgatgtg gtttggggg ccaagtctgt acaacatctt | 780 |
| gagtcccttt atgccgctgt taccaatttt cttttgtctt gggtataca tttaaaccct | 840 |
| cacaaaacaa aaagatgggg atattcccct aacttcatgg gatatgtaat gggagttgg | 900 |
| ggcacattgc cacaggaaca tattgtacaa aaaatcaaaa tgtgttttag gaaacttcct | 960 |
| gtaaacaggc ctattgattg gaaagtatgt caacgaattg tgggtctttt ggggtttgcc | 1020 |
| gcccctttca cgcaatgtgg atatcctgct ttaatgcctt tatatgcatg tatacaagca | 1080 |
| aaacaggctt ttactttctc gccaacttac aaggcctttc taagtaaaca gtatctgaac | 1140 |
| ctttaccccg ttgctcggca acggcctggt ctgtgccaag tgtttgctga cgcaaccccc | 1200 |
| actggttggg gcttggccat aggccatcag cgcatgcgtg gaacctttgt gtctcctctg | 1260 |
| ccgatccata ctgcggaact cctagccgct tgttttgctc gcagcaggtc tggggcaaaa | 1320 |
| ctcatcggga ctgacaattc tgtcgtgctc tcccgcaagt atacatcatt tccatggctg | 1380 |
| ctaggctgtg ctgccaactg gatcctgcgc gggacgtcct tgtttacgt cccgtcggcg | 1440 |
| ctgaatcccg cggacgaccc ctcccggggc cgcttgggc tctaccgccc gcttctccgc | 1500 |
| ctgttgtacc gaccgaccac ggggcgcacc tctctttacg cggactcccc gtctgtgcct | 1560 |
| tctcatctgc cggaccgtgt gcacttcgct tcacctctgc acgtcgcatg gagaccaccg | 1620 |
| tgaacgccca caggaacctg cccaaggtct tgcataagag gactcttgga ctttcagcaa | 1680 |
| tgtcaacgac cgaccttgag gcatacttca aagactgtgt gtttaatgag tgggaggagt | 1740 |

```
tgggggagga ggttaggtta aaggtctttg tactaggagg ctgtaggcat aaattggtgt    1800
gttcaccagc accatgcaac tttttcacct ctgcctaatc atctcatgtt catgtcctac    1860
tgttcaagcc tccaagctgt gccttgggtg gctttggggc atggacattg acccgtataa    1920
agaatttgga gcttctgtgg agttactctc ttttttgcct tctgacttct ttccttctat    1980
tcgagatctc ctcgacaccg cctctgctct gtatcgggag gccttagagt ctccggaaca    2040
ttgttcacct caccatacgg cactcaggca agctattctg tgttggggtg agttgatgaa    2100
tctagccacc tgggtgggaa gtaatttgga agatccagca tccagggaat tagtagtcag    2160
ctatgtcaac gttaatatgg gcctaaaaat cagacaacta ttgtggtttc acatttcctg    2220
tcttactttt gggagagaaa ctgttcttga atatttggtg tcttttggag tgtggattcg    2280
cactcctcct gcatatagac caccaaatgc ccctatctta tcaacacttc cggaaactac    2340
tgttgttaga cgaagaggca ggtcccctag aagaagaact ccctcgcctc gcagacgaag    2400
gtctcaatcg ccgcgtcgca gaagatctca atctcgggaa tctcaatgtt agtattcctt    2460
ggacacataa ggtgggaaac tttacggggc tttattcttc tacggtacct tgctttaatc    2520
ctaaatggca aactccttct tttcctgaca ttcatttgca ggaggacatt gttgatagat    2580
gtaagcaatt tgtggggccc cttacagtaa atgaaaacag gagactaaaa ttaattatgc    2640
ctgctaggtt ttatcccaat gttactaaat atttgccctt agataaaggg atcaaaccgt    2700
attatccaga gtatgtagtt aatcattact ccagacgcg acattattta cacactcttt    2760
ggaaggcggg gatcttatat aaaagagagt ccacacgtag cgcctcattt tgcgggtcac    2820
catattcttg gaacaagat ctacagcatg ggaggttggt cttccaaacc tcgaaaggc     2880 atggggacaa atctttctgt ccccaatccc ctgggattct tccccgatca tcagttggac    2940
cctgcattca aagccaactc agaaaatcca gattgggacc tcaacccgca caaggacaac    3000
tggccggacg ccaacaaggt gggagtggga gcattcgggc cagggttcac ccctccccat    3060
gggggactgt tggggtggag ccctcaggct cagggcctac tcacaactgt gccagcagct    3120
cctcctcctg cctccaccaa tcggcagtca ggaaggcagc ctactccctt atctccacct    3180
ctaagggaca ctcatcctca ggccatgcag tggaa                              3215
```

<210> SEQ ID NO 12
<211> LENGTH: 226
<212> TYPE: PRT
<213> ORGANISM: Hepatitis B virus

<400> SEQUENCE: 12

```
Met Glu Asn Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Ala Pro Thr Cys
            35                  40                  45

Pro Gly Gln Asn Ser Gln Ser Pro Thr Ser Asn His Ser Pro Thr Ser
        50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Leu Pro Gly
                100                 105                 110
```

```
Thr Ser Thr Thr Ser Thr Gly Pro Cys Lys Thr Cys Thr Ile Pro Ala
        115             120             125

Gln Gly Thr Ser Met Phe Pro Ser Cys Cys Cys Thr Lys Pro Ser Asp
        130             135             140

Gly Asn Cys Thr Cys Ile Pro Ile Pro Ser Ser Trp Ala Phe Ala Arg
145             150             155             160

Phe Leu Trp Glu Trp Ala Ser Val Arg Phe Ser Trp Leu Ser Leu Leu
                165             170             175

Val Pro Phe Val Gln Trp Phe Val Gly Leu Ser Pro Thr Val Trp Leu
                180             185             190

Ser Val Ile Trp Met Met Trp Tyr Trp Gly Pro Ser Leu Tyr Asn Ile
        195             200             205

Leu Ser Pro Phe Leu Pro Leu Leu Pro Ile Phe Phe Cys Leu Trp Val
        210             215             220

Tyr Ile
225
```

HEPATITIS B VIRUS MUTANT, MUTANT AMPLIFICATION KIT AND USE THEREOF

CROSS REFERENCE TO RELATED PATENT APPLICATION

The present application is the US national stage of PCT/CN2012/071108 filed on Feb. 14, 2012, which claims the priorities of the Chinese patent applications No. 201110384731.7 filed on Nov. 28, 2011, which applications are incorporated herein by reference.

BACKGROUND OF THE PRESENT INVENTION

Field of Invention

The present invention relates to the field of biotechnology, in particular to a new hepatitis B virus mutation, mutant amplification kit and use thereof.

Description of Related Arts

By the current global estimates, there are 350 million chronic hepatitis B virus (HBV) carriers, and one-third of the global population infected with HBV. In China, Hepatitis B is one of the most serious, and most extensive infectious diseases, with the infection rate as high as 60%, and about 120 million people carry HBV. The incidence of hepatitis B ranks first in infectious diseases, and the mortality ranks third in infectious disease.

According to the different clinical manifestations of HBV infection, it can be divided into several types: asymptomatic carrier state, acute self-limited hepatitis, chronic hepatitis, fulminant hepatitis (FH). Mother-to-child transmission is a major route of transmission of HBV, the patient is usually in a state of immune tolerance, and the response to HBV does not occur, but most asymptomatic carriers tend to occur hepatitis, and even some eventually grows into FH. The mechanism of Hepatitis B aggravation has not been cleared by now, and is currently considered on account of two aspect, which are function of host immune and function of virus. The occurrence of HBV variation and severe hepatitis remains controversial, and there is no one gene variant can be acted as a symbol variant of severe hepatitis B. Moreover, a large number of studies have shown that HBV exists in the form of quasispecies in the patient's body, and the quasispecies characteristics of HBV should be taken into account as studying the relationship between virus mutation and hepatitis. Currently, most studies investigate HBV quasispecies by PCR-cloning-sequencing method. Therefore, it would offer help for the clinical early diagnosis and intervention of HBV, to find gene loci with closely related to hepatitis aggravation.

SUMMARY OF THE PRESENT INVENTION

The object of the present invention is to provide a hepatitis B virus mutant with closely related to hepatitis aggravation, a mutant amplification kit, and its application, to offer help for the clinical early diagnosis and intervention of HBV.

One aspect of the invention discloses a hepatitis B virus (referred to as hepatitis B virus or HBV) mutant, including hepatitis B virus genome, a mutation of the hepatitis B virus mutant occurs in genome sequence No. 216 and/or 285 of the hepatitis B virus, the mutation occurred at position 216 is that base T mutates to C (216T→C), the mutation occurred at position 285 is that base G mutates to A (285G→A).

Preferably, the nucleotide sequence of the hepatitis B virus genome is selected from SEQ ID NO:1, SEQ ID NO:10 or SEQ ID NO: 11.

Further, in the complementary sequence of the HBV genome sequence of the hepatitis B virus mutant, the mutation occurred at the corresponding genomic locus to genome No. 216 is that A mutates to G, and the mutation occurred at the corresponding genomic locus to genome No. 285 is that C mutates to T.

Preferably, compare to the normal S protein of hepatitis B virus, the S protein encoded by the hepatitis B virus mutant features that its amino acid sequence occurs mutation at position 21 and/or 44, the amino acid mutation at position 21 is mutating from leucine (L) to serine (S), and the amino acid mutation at position 44 is mutating from glycine (G) to glutamic acid (E).

More preferably, the amino acid sequence of the normal S protein of the hepatitis B virus is SEQ ID NO: 12.

MENTTSGFLGPLLVLQAGFFLLTRILTIPQSLDSW-WTSLNFLGGAPTCPGQNS QSPTSNHSPTSCPPICP-GYRWMCLRRFIIFLFILLLCLIFLLVLLDYQGMLPVC-PLLPGTS TTSTGPCKTCTIPAQGTSMFPSCCCTKPSDGNCTCIP-IPSSWAFARFLWEWASVRFSWL SLLVPFVQWFVGL-SPTVWLSVIWMMWYWGPSLYNILSPFLPLLPIFFCL-WVYI (SEQ ID NO:12)

The second aspect of the present invention discloses a HBV mutant amplification kit for amplifying the gene fragments of the hepatitis B virus genome sequence No. 216 and No. 285, including primers, dNTP, PCR buffer, DNA polymerization enzyme, and ddH$_2$O, the primers includes an upstream primer and a downstream primer, the primer specific amplifying the gene fragments including the hepatitis B virus genome sequence No. 216 and No. 285.

Preferably, the DNA polymerization enzyme is a high fidelity DNA polymerization enzyme; more preferably, the high fidelity DNA polymerization enzyme is Prime Star.

Preferably, PCR buffer solution is 5× Prime Star buffer.

Preferably, the sequences of the upstream primer and downstream primer are as follows:

| primer | sequence |
| --- | --- |
| upstream primer | 5'-ggagcgggagcattcgg-3' (SEQ ID NO: 8) |
| downstream primer | 5'-ataaaacgccgcagasacatccagc3' (SEQ ID NO: 9) |

The PCR system of the kit of the present invention is as follows:

| | |
| --- | --- |
| DNA template | 2 µL |
| Upstream primer | 1 µL |
| Downstream primer | 1 µL |
| dNTP (concentration of the four dNTP is 2.5 mM, respectively) | 4 µL |
| 5 × Prime Star buffer (Mg$^{2+}$ Plus) | 10 µL |
| Prime Star (5 U/µL) | 0.5 µL |

Dilute with ddH$_2$O to the total volume of 50 µL.

Preferably, the kit of the present invention may also include DNA extraction reagent.

Preferably, the amplification procedure of the HBV mutant amplification kit of the invention is: predenaturation at 94° C. 3 min, then 94° C. 30 s, 57° C. 15 s, 72° C. 2 min for 45 cycles, extending at 72° C. for 10 min.

The third aspect of the present invention discloses a usage for the HBV mutant amplification kit in the following steps:

1) Preparation of DNA template: drawing the peripheral venous blood and extracting HBV genome as the DNA template;

2) PCR amplification: performing PCR amplification reaction of the DNA template as prepared in step 1) according to the above amplification procedure by the kit of the present invention;

3) Purifying PCR product: PCR product is recycled and purified via agarose gel electrophoresis.

Preferably, the amplification procedure in step 2) is: predenaturation at 94° C. 3 min, then 94° C. 30 s, 57° C. 15 s, 72° C. 2 min for 45 cycles, extending at 72° C. for 10 min.

Preferably, the concentration of the agarose gel electrophores used in step 2) is 1%.

The purified PCR product obtained by step 3) is sequenced by sanger sequencing technology or solexa sequencing technology, the sequencing results are compared with the sequence of SEQ ID NO: 1, SEQ ID NO: 10 or SEQ ID NO: 11, to confirm that whether the gene fragments of the hepatitis B virus genome sequence No. 216 and No. 285 corresponding to the PCR product exists the mutation of the present invention.

The fourth aspect of the present invention discloses a use of hepatitis B virus mutant or HBV mutant amplification kit in the preparation of a medicament for the clinical early diagnosis and prevention of the severe hepatitis B disease.

The fifth aspect of the present invention further discloses a method for clinical early diagnosis and prevention of the severe hepatitis B disease, to detect whether the subject blood has the hepatitis B virus mutant of the present invention.

Preferably, in the method for the clinical early diagnosis and prevention of the severe hepatitis B disease, the steps to detect whether the subject blood has the hepatitis B virus mutant are as follows:

1) Preparation of DNA template: drawing the peripheral venous blood of the test subject and extracting HBV genome as the DNA template;

2) PCR amplification: adding the DNA template as prepared in step 1) into the PCR reaction system, amplifying the gene fragments including the hepatitis B virus genome sequence No. 216 and No. 285;

3) Purifying PCR product: PCR product is recycled and purified via agarose gel electrophoresis;

4) Sequencing of the PCR product: the PCR product by purified and obtained by step 3) is sequenced by the gene sequencing technology;

5) Result analysis: the sequencing results of step 4) are compared with the sequence of SEQ ID NO: 1, SEQ ID NO: 10 or SEQ ID NO: 11, to confirm that whether the hepatitis B virus genome sequence No. 216 and No. 285 corresponding to the PCR product exists mutation.

More preferably, the PCR reaction system in the step 2) includes primers, dNTP, PCR buffer, DNA polymerization enzyme, and ddH$_2$O, the primers includes an upstream primer and a downstream primer, amplifying the gene fragments including the hepatitis B virus genome sequence No. 216 and No. 285.

More preferably, the primer sequence is SEQ ID NO: 8-9.

More preferably, the DNA polymerization enzyme is a high fidelity DNA polymerization enzyme; optimally, the high fidelity DNA polymerization enzyme is Prime Star.

More preferably, PCR buffer solution is 5× Prime Star buffer.

More preferably, the amplification procedure in step 2) is: predenaturation at 94° C. 3 min, then 94° C. 30 s, 57° C. 15 s, 72° C. 2 min for 45 cycles, extending at 72° C. for 10 min.

More preferably, the gene sequencing technology in step 4) is sanger sequencing technology or solexa sequencing technology.

More preferably, the mutation occurred at position 216 of the hepatitis B virus genome sequence corresponding to the PCR product is that base T mutates to C, the mutation occurred at position 285 of the hepatitis B virus genomic sequence corresponding to the PCR product is that base G mutates to A.

The test subject that contains the mutant of the present invention in the blood tends to occur serious inflammation of the liver.

The mutation of NO. 216 (216T→C) and the mutation of NO. 285 (285G→A) of the hepatitis B virus genome sequence are closely related to the inflammation aggravation of the hepatitis B.

Since HBV in patient's body is in the form of quasispecies, and its genotype has a comparatively high mutation rate in humans, therefore, the present invention adopts the solexa high-throughput sequencing technology to detect complete HBV genome for screening out the loci closely associated with the hepatitis aggravation; and provides a HBV mutant amplification kit to perform amplification on the HBV genome carried by the hepatitis B patient via the designed specific primers, and to compare the sequences of the amplification products with the sequence of SEQ ID NO:1, SEQ ID NO:10 or SEQ ID NO:11 via gene sequencing method to detect whether T→C mutation at position 216 and/or G→A mutation at position 285 exists in the sample to be detected, thereby offering help for the clinical early diagnosis and intervention of severe hepatitis B, and providing references for further study on the functional changes caused by HBV gene mutation.

DETAILED DESCRIPTION OF THE PREFERRED EMBODIMENTS

Figure 1:
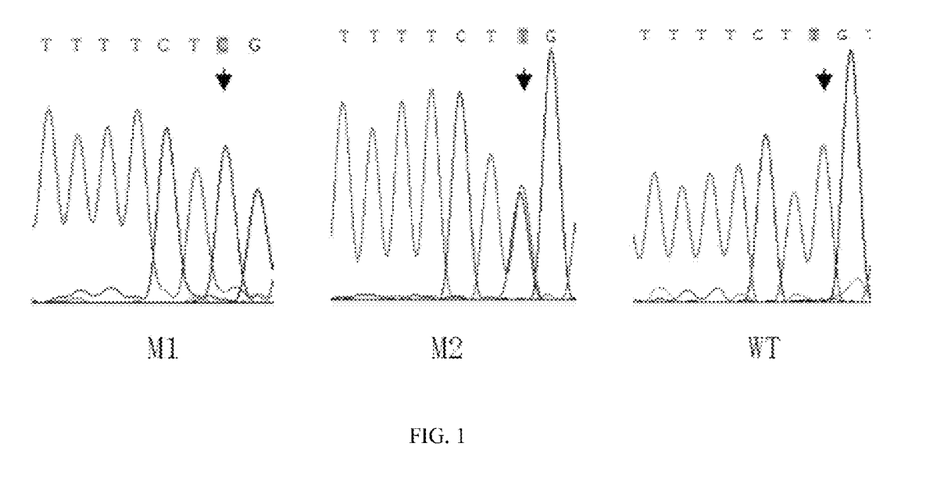
FIG. 1: M1 is that the locus T in HBV 216 of a patient mutates to C, M2 is that the loci T and C coexist in HBV 216 of a patient, WT is that the locus in HBV 216 of a patient does not occur mutation.
Figure 2:
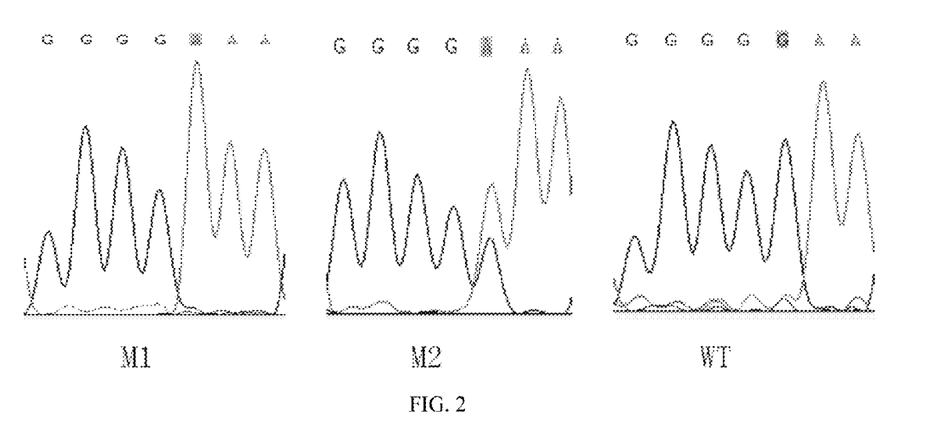
FIG. 2: M1 is that the locus G in HBV 285 of a patient mutates to A, M2 is that the loci G and A coexist in HBV 285 of a patient, WT is that the locus in HBV 285 of a patient does not occur mutation.

The present invention is further illustrated by combining with the specific embodiments. It should be understood that the following embodiments are merely used to explain the invention, but are not used to limit the scope of the invention.

First Embodiment

First: Serum Collection from Patients with Severe Hepatitis B and Chronic Hepatitis B Collect the serum samples of 12 cases with severe hepatitis B and 12 cases with chronic mild hepatitis B from the first affiliated hospital of medical school of Zhejiang university (the patients has been diagnosed explicitly with severe or chronic mild hepatitis B by the indicators of ALT, AST, TBIL, PT, viral titer, etc., and clinical manifestations)

Second: Primer Design

We download 616 complete sequences of HBV genome, and design three pairs of primers (SEQ ID NO: 2, SEQ ID NO: 3, SEQ ID NO:4, SEQ ID NO:5, SEQ ID NO:6, SEQ ID NO:7) by using primer 5.0 software according to the complete genome conserved sequence of HBV.

Third: HBV DNA Extraction

An equal volume of nucleic acid extract is added into the 50 ul serum and mixed, followed by water bath at 100 for 10 min, centrifugation for 10 min with 13000 r/min, and then the supernatant is drawn for PCR amplification.

Fourth: PCR Amplification

The amplification for the HBV gene of a patient adopts Prime Star fidelity enzymes of TaKaRa Company, with the brief steps as follows: total volume of the PCR reaction 50 μL, wherein template DNA 2 μL, upstream primer and downstream primer (10 uM) 1 μL, respectively, dNTP (2.5 mM for each four dNTP) 4 μL, 5× Prime Star buffer ($Mg^{2+}$ Plus) 10 μL, Prime Star (5 U/ul) 0.5 μL, and dilute with $ddH_2O$ to the total volume of 50 μL. Cycle parameters: predenaturation at 94° C. 3 min, then 94° C. 30 s, 57° C. 15 s, 72° C. 2 min for 45 cycles, extending at 72° C. for 10 min. The product is recycled and purified via agarose gel electrophoresis with the concentration of 1%.

Meanwhile, take the expression plasmid HBV1.37 which contained HBV 1.3-fold complete sequence in laboratory as a template, to amplify the above three pieces of HBV gene segment. The product is recycled and purified via agarose gel electrophoresis with the concentration of 1%, for the quality control of the high-throughput sequencing.

Fifth: Sanger Sequencing

The purified PCR product performs sanger sequencing, and three fragments is pieced for a whole HBV DNA complete sequence by DNASTAR software.

Sixth: Solexa High-Throughput Sequencing and Data Analysis Method

Sequencing method: the purified PCR product is sequenced by nano institute, Zhejiang university, the experiment process is briefly described as follows: 1, the genomic DNA is disrupted into small fragments of 200 bp, both ends of each fragment add connectors (each sample add a specific connector). 2, DNA fragments are purified by QIAGEN gel extraction kit. 3, PCR amplifies the DNA fragment with connectors and is purified. 4, detected by Solexa high-throughput sequencing platform.

Data Analysis (1) Splicing of Sequencing Fragment (Mapping)

Obtain the sequence (reads, tags) data of each sample by the high-throughput sequencing, firstly the sequence data in both directions is composed into a file, and then is spliced into a complete HBV genome by using bowtie software. The Chinese HBV genome standard type B and C sequences reported in "Profile of public nucleotide databases HBV complete genome sequence and establishment of Chinese HBV reference sequence" (Progress in Natural Science 2008, 18 (2)) acts as splicing reference sequence (SEQ ID NO: 1, SEQ ID NO: 10, SEQ ID NO: 11), while a length of sequence is extracted before and after the gap of the linear genome to compose into a short fragment and the reference sequence is added as well, to ensure the sequence covering on the gap can be correctly spliced. Parameter is set as: seed length=30, allowable mismatch=3. Since according to the principle of high-throughput sequencing, the results of the previous test has the highest accuracy, with the sequencing length increases, the accuracy decreases, thus we choose the first 30 bases for comparison, the sequence with more than three mutations is considered as a sequence with relatively poor sequencing quality, and is removed (i.e., every 10 bases allow a mutation)

(2) Statistical Tests of the Composition Difference of Bases at Each Locus

Perform statistics on the sequence of the splicing file of each sample and its coordinate read in the genome, to obtain the absolute number of the four types of bases measured in all base positions of the complete genome. Then each sample of the severe hepatitis B group and mild hepatitis B group are compared in turn by using combination method. Obtain the base type with significant difference in each locus between two samples (p<0.001) by applying Chi-square test; perform statistics on the above information in all comparison pairs, and take the base type detected with significant difference in more than a half of comparison pairs, while without opposite significant proportion change of base at a certain locus in any comparison pair as the base change with significant difference between the severe hepatitis B group and mild hepatitis B group, and remains (the above steps are completed by writing a script by Python program language (www.python.org).

Through the statistical analysis of the sequencing results of the severe hepatitis B and mild hepatitis B, two new mutation loci are found that: 216T→C and 285G→A. For the 12 cases of severe hepatitis patients, 10 cases exist 216T→C mutation, while 9 cases exist 285G→A mutation.

Though Solexa high-throughput sequencing, it has been detected that, in the severe hepatitis patients with 216T→C mutation, the proportion of 216T→C mutant strain is 8% to 100%; while in the severe hepatitis patients with 285G→A mutation, the proportion of 285G→A mutant strain is 11% to 100%. In the 12 cases of severe hepatitis patients, only 1 case exists duplex mutation of 216T→C and 285G→A, and the proportion of 216T→C mutant strain and 285G→A mutant strain is 17% and 7%, respectively. Further, it is found that in this experiment, when the proportion of 216T→C mutant strain is less than 17%, and the proportion of 285G→A mutant strain is less than 11%, those mutant strains are unable to be detected by conventional sanger sequencing method, such that this type of case is unable to be detected as well.

The results showed that, the solexa high-throughput sequencing technology features much better sensitivity of mutation detection than that of the conventional sanger sequencing, and enables to find the non-dominant strains existed in HBV patients, and is beneficial for us to study the complex quasispecies characteristics in patients. While sanger sequencing method is reliable, accurate, and forms large scale, and is still a best choice for a small number of sequences, thereby commonly being used for the sequencing of PCR products, terminal sequencing of the plasmids and bacterial artificial chromosomes.

In addition, the majority of patients with severe hepatitis have 216T→C and 285G→A mutations, the mutations of the two loci results in a change of amino acid of HBV S region, as shown in the table below:

| Mutation of nucleotide | Mutation position | Mutation of amino acid |
|---|---|---|
| 216T→C | HBV S region, P region | No change in P region, S protein 21L→S |
| 285G→A | HBV S region, P region | No change in P region, S protein 44G→E |

Therefore, 216T→C and 285G→A mutations of hepatitis B virus may be related with the onset of severe hepatitis, further research would offer help for clinical early intervention and diagnostic.

Second Embodiment

First: Serum Collection in Patients with Hepatitis B

Collect serum samples of hepatitis B cases from a plurality of domestic hospitals, wherein there are 102 cases with severe hepatitis B, 127 cases with chronic mild hepatitis B, 95 cases with chronic moderate and severe hepatitis B and 65 cases of carriers (the patients has been diagnosed explicitly with hepatitis B by the indicators of ALT, AST, TBIL, PT, viral titer, etc., and clinical manifestations))

Second: Primer Design

We download 616 complete sequences of HBV genome, and design a pair of primer (SEQ ID NO: 8, SEQ ID NO: 9) by using primer 5.0 software according to the complete genome conserved sequence of HBV, to amplify a length of gene fragment including No. 216 and No. 285 of the HBV genome sequence.

Third: Preparation of Kit

Assemble the above primer (SEQ ID NO: 8, SEQ ID NO: 9) and dNTP, 5× Prime Star buffer, Prime Star, ddH$_2$O for a HBV mutant amplification kit.

Fourth: HBV DNA Extraction

An equal volume of nucleic acid extract is added into the 50 ul serum and mixed, followed by water bath at 100 for 10 min, centrifugation for 10 min with 13000 r/min, and then the supernatant is drawn for PCR amplification.

Fifth: PCR Amplification

The brief steps of the amplification for the HBV gene of a patient are as follows: total volume of the PCR reaction 50 μL, wherein template DNA 2 μL, primers (10 uM) 1 μL, respectively, dNTP (2.5 mM for each) 4 μL, 5× Prime Star buffer ($Mg^{2+}$ Plus) 10 μL, Prime Star (5 U/ul) 0.5 μL, and dilute with $ddH_2O$ to the total volume of 50 μL. Cycle parameters: predenaturation at 94° C. 3 min, then 94° C. 30 s, 56° C. 15 s, 72° C. 50 s for 45 cycles, extending at 72° C. for 10 min. The product is recycled and purified via agarose gel electrophoresis with the concentration of 1%.

Sixth: Sanger Sequencing

The purified PCR product performs sequencing according to the conventional sanger sequencing technique in the art.

Seventh: Statistical Method Apply Nonparametric Rank Sum Test, p<0.05 is Considered as a Statistically Significant Difference.

Eighth: Experimental Result

Specific experimental results are shown in Table 1-3. The data from table 1 and table 2 show that: the incidence of 216T→C mutation in patients with severe hepatitis is 45% (46/102), while the incidence of 285G→A mutation is 39% (40/102); loci mutation frequency of 216T→C in patients with chronic moderate and severe hepatitis is 23% (22/95), while the incidence of 285G→A mutation is 29% (28/95); loci mutation frequency of 216T→C in patients with chronic mild hepatitis is 8% (10/127), while the incidence of 285G→A mutation is 5% (6/127); loci mutation frequency of 216T→C in hepatitis B carriers is 5% (3/65), while 285G→A mutation is not found. Compare the hepatitis disease between the mutational sample and non-mutational sample by applying nonparametric rank sum test, showing the result of P<0.001, which indicates that mutational case tends to occur severe inflammation of the liver.

TABLE 1

Distribution of 216T→C mutation in the four groups of patients with hepatitis B

| 216T→C mutation | Mutational sample | Wild sample | Total sample | Mutation rate |
|---|---|---|---|---|
| Severe hepatitis B | 46 | 56 | 102 | 45% |
| chronic moderate and severe hepatitis B | 22 | 73 | 95 | 23% |
| chronic mild hepatitis B | 10 | 117 | 127 | 8% |
| hepatitis B carrier | 3 | 62 | 65 | 5% |

Note:
Compare the hepatitis disease between the mutational sample and non-mutational sample by applying nonparametric rank sum test, showing the result of P <0.001.

TABLE 2

Distribution of 285G→A mutation in the four groups of patients with hepatitis B

| 285G→A mutation | Mutational sample | Wild sample | Total sample | Mutation rate |
|---|---|---|---|---|
| Severe hepatitis B | 40 | 62 | 102 | 39% |
| chronic moderate and severe hepatitis B | 28 | 67 | 95 | 29% |
| chronic mild hepatitis B | 6 | 121 | 127 | 5% |
| hepatitis B carrier | 0 | 65 | 65 | 0% |

Note:
Compare the hepatitis disease between the mutational sample and non-mutational sample by applying nonparametric rank sum test, showing the result of P <0.001.

TABLE 3

Distribution of 216T→C/285G→A duplex mutation in the four groups of patients with hepatitis B

| 216T→C/285G→A duplex mutation | Mutational sample | Wild sample | Total sample | Mutation rate |
|---|---|---|---|---|
| Severe hepatitis B | 32 | 70 | 102 | 31% |
| chronic moderate and severe hepatitis B | 15 | 80 | 95 | 16% |
| chronic mild hepatitis B | 5 | 122 | 127 | 4% |
| hepatitis B carrier | 0 | 65 | 65 | 0% |

Note:
Compare the hepatitis disease between the mutational sample and non- mutational sample by applying nonparametric rank sum test, showing the result of P <0.001.

Table 3 shows that: the incidence of 216T→C/285G→A dual mutation in patients with severe hepatitis is 31% (32/102), the incidence in patients with chronic moderate and severe hepatitis is 16% (15/95), the incidence in patients with chronic mild hepatitis is 4% (5/127), and the incidence in carriers is 0%; nonparametric rank sum test shows P<0.001, the experimental data indicate that 216T→C/285G→A duplex mutational case tends to have severe inflammation of the liver.

The experimental results show that: the 216T→C and 285G→A mutations are closely related to the aggravated liver inflammation, and their further study is beneficial for clarifying the molecular mechanism of hepatitis B aggravation and has positive significance for clinical early warning of severe hepatitis.

What is claimed is:

1. A kit for identifying hepatitis B (HBV) genetic mutants, wherein the kit comprises:
   a) two primers, wherein the two primers consist of the sequences of SEQ ID NO:8 and SEQ ID NO:9,
   b) dNTP,
   c) PCR buffer,
   d) DNA polymerization enzyme, and
   e) ddH$_2$0,
   wherein the kit provides for the identification of mutations in the HBV genome at positions 216 and/or 285 relative to SEQ ID NO:1, SEQ ID NO:10, or SEQ ID NO:11.

2. The kit according to claim 1, wherein the DNA polymerization enzyme is a high fidelity DNA polymerization enzyme.

3. The kit according to claim 1, wherein the amplification procedure of the kit is:
   a) pre-denaturation at 94° C. for 3 minutes,
   b) amplification for 45 cycles of the following:
      I) 94° C. for 30 seconds
      II) 57° C. for 15 seconds,
      III) 72° C. for 2 minutes, and after the amplification cycles are complete,
   c) extending for 72° C. for 10 minutes.

4. A method for early clinical diagnosis and prevention of severe hepatitis B disease by determining whether a subject's blood comprises a hepatitis B virus (HBV) mutant, wherein the hepatitis B virus mutant comprises a mutation of the HBV genome at position 216 and/or 285 of the HBV according to SEQ ID NO:1, SEQ ID NO:10, or SEQ ID NO:11, wherein said mutation at position 216 is a T to C substitution and wherein, said mutation at position 285 is a G to A substitution, wherein the steps to detect whether the subject's blood comprises said HBV mutant are:
   1) preparation of the HBV genomic DNA template by drawing the peripheral venous blood of the test subject and extracting HBV genomic DNA from said blood;
   2) amplifying the DNA template acquired in step 1) through PCR amplification in a PCR reaction system to amplify the gene fragments comprising position 216 and 285 from the HBV genome to obtain a PCR product, wherein the PCR reaction system comprises an upstream and downstream primer pair, wherein the upstream and downstream primer pair are SEQ ID NO:8 and 9, respectively;
   3) purifying the resulting PCR product from step 2;
   4) sequencing the PCR product purified and obtained from step 3);
   5) analyzing the results by comparing the sequencing results of step 4) with the sequence of SEQ ID NO:1, SEQ ID NO:10, and/or SEQ ID NO:11 to confirm whether the PCR product comprises a mutation in the HBV genome at position 216 and/or 285; wherein presence of the mutation at position 216 and/or 285 allows the subject to have clinical early diagnosis and/or intervention for severe hepatitis B disease.

5. The method according to claim 4, wherein the PCR reaction system in step 2) further comprises:
   a) dNTP mix,
   b) PCR buffer,
   c) DNA polymerization enzyme, and
   d) ddH$_2$0.

6. The method according to claim 4, wherein the amplification procedure of step 2) is as follows:
   a) pre-denaturation at 94° C. for 3 minutes,
   b) amplification for 45 cycles of the following:
      I) 94° C. for 30 seconds
      II) 57° C. for 15 seconds,
      III) 72° C. for 2 minutes, and after the amplification cycles are complete,
   c) extending for 72° C. for 10 minutes.

* * * * *